United States Patent [19]

Su et al.

[11] Patent Number: 5,296,602
[45] Date of Patent: Mar. 22, 1994

[54] MULTISUBSTITUTED 1-HYDROXY-9-ACRIDONES WITH ANTICANCER ACTIVITY

[75] Inventors: Tsann-Long Su, Baldwin Place; Kyoichi A. Watanabe, Rye Brook, both of N.Y.

[73] Assignee: Sloan-Kettering Institute for Cancer Research, New York, N.Y.

[21] Appl. No.: 671,126

[22] Filed: Mar. 18, 1991

[51] Int. Cl.⁵ .............................. C07C 63/42
[52] U.S. Cl. .................... 546/103; 562/433; 568/630
[58] Field of Search .................. 546/103; 514/290

[56] References Cited

U.S. PATENT DOCUMENTS 4,691,059 9/1987 Mita et al. ..................... 546/103

FOREIGN PATENT DOCUMENTS 1414621 12/1972 United Kingdom .

OTHER PUBLICATIONS

Su, T. L., et al., *Tetrahedron Letters*, vol. 32, No. 12, pp. 1541–1544 (Mar. 18, 1991).
Chou, T. C., et al., *Preclin. Pharm./Exper. Therapeutics*, vol. 32, p. 403, abstract No. 2395 (Mar. 1991).
Chou, T. C., et al., *Preclin. Pharm./Exper. Therapeutics*, vol. 30, p. 608, abstract No. 2422, (Mar. 1989).
Chou, T. C., et al., *Phytotherapy Research*, vol. 3, pp. 237–242 (1989).

*Primary Examiner*—Nicholas S. Rizzo
*Attorney, Agent, or Firm*—John P. White

[57] ABSTRACT

The present invention provides a compound having the structure:

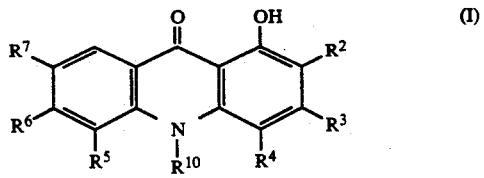

The present invention also provides a method for synthesizing a compound having the above-identified structure as well as the intermediate compounds produced according to that method. The present invention further provides a pharmaceutical composition comprising the above compounds. Lastly, the present invention provides a method of inhibiting growth of tumor cells.

17 Claims, No Drawings

MULTISUBSTITUTED 1-HYDROXY-9-ACRIDONES WITH ANTICANCER ACTIVITY

The invention described herein was made in the course of work under Grant Nos. CA08748 and CA18856 from the National Cancer Institute, National Institutes of Health, U.S. Department of Health and Human Services. The U.S. Government has certain rights in this invention.

BACKGROUND OF THE INVENTION

Throughout this application, various publications are referenced. The disclosures of these publications in their entirety are hereby incorporated by reference into this application in order to more fully describe the state of the art as known to those skilled therein as of the date of the invention described and claimed herein.

Several 9-acridones have been found to exhibit anticancer activity. 9-Acridone derivatives with or without a dialkylaminoalkyl side chain attached to the N-position were synthesized and studied for their antitumor activity (Radzikowski et al., *Archvm. Immunol. Ther. Exp.* 1971; 19: 219). Among these, N-(N-dialkylamino)ethyl-1-nitro-9-acridones were shown to have antitumor activity in the S-180 system in vivo and these have undergone extensive preclinical testing (Pelczarska et al., *Archvm. Immumnol. Ther. Exp.* 1973; 22: 823). It Was also reported that the bis-cationic side-chain substituted 9-acridone can act as an acceptable chromophore for DNA intercalation. (Wright et al., *Biochemistry* 1980; 19: 5825).

Recently, the structure-activity relationships of fifty natural acridone alkaloids for their effects on the inhibition of cell growth and macromolecule biosynthesis of human promyelocytic leukemic cells has been studied. (Chou et al., *Phytotherapy Res.* 1989; 3: 237). It was found that twenty three out of the fifty alkaloids were more active than acronycine, an antineoplastic alkaloid used in clinical trails (Svoboda et al., *J. Pharm. Sci.* 1966; 55: 758–768). For inhibition of cell growth of human leukemic HL-60 cell lines in vitro, the most potent compound in this series was TSA-35 (1,6-dihydroxy-2,3,4,5-tetramethoxy-10-methyl-9-acridone, or glyfoline), with $IC_{50}$ of 1.1 μM. TSA-35 was originally isolated from *Glycosmic citrifolia* (Wild.) Lindl. (Rutaceae) in a minute amount by Wu et al. (Wu, T. S. and Furukawa, H., *Heterocycles* 1982; 19: 1047). It has not been reported to date that the known natural alkaloid, 1,6-hydroxy-2,3,4,5-tetramethoxy-9-acridone exhibits antitumor activity. The chemical synthesis of this alkaloid and structurally similar compounds also has not been reported to date.

SUMMARY OF THE INVENTION

The present invention provides a compound having the structure:

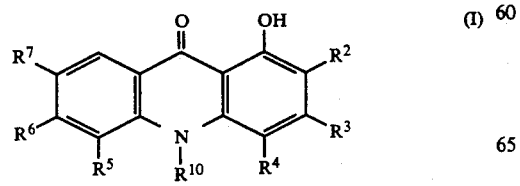

(I)

wherein $R^2$ and $R^3$ are the same or different and are hydrogen, a saturated or unsaturated alkyl group having 1 to 5 carbon atoms, a hydroxy group, a saturated or unsaturated alkyloxy group having to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-acyl group, an O-aroyl group, or an O-aryl group;

$R^4$ is hydrogen, a saturated or unsaturated alkyl group having 1 to 5 carbon atoms, a hydroxy group, a hydroxymethyl group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-alkyloxyalkyloxyalkyl group wherein each alkyl is the same or different having 1 to 5 carbon atoms, an O-acyl group, an O-aroyl group, or an O-aryl group;

$R^5$, $R^6$, and $R^7$ are the same or different and are hydrogen, a saturated or unsaturated alkyl group having 1 to 5 carbon atoms, sulfate, phosphate, a hydroxy group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-acyl group, an O-aroyl group, an O-aryl group, a nitro group, an amino group, an N-alkylamino group having 1 to 5 carbon atoms, an N,N-dialkylamino group with each alkyl having 1 to 5 carbon atoms, an aminoalkyloxy group having 1 to 5 carbon atoms, an N-alkyl-aminoalkyloxy group wherein each alkyl is the same or different having i to 5 carbon atoms, an N,N-dialkyl-aminoalkyloxy group wherein each alkyl is the same or different having 1 to 5 carbon atoms, a quaternary ammonium alkyloxy salt, or a halogen; and $R^{10}$ is hydrogen, a saturated or unsaturated alkyl group having 1 to 5 carbon atoms, an aminoalkyl group having 1 to 5 carbon atoms, an N-alkylaminoalkyl group wherein each alkyl is the same or different having 1 to 5 carbon atoms, an N,N-dialkylaminoalkyl group wherein each alkyl is the same or different having 1 to 5 carbon atoms, or an amino acid moiety.

The present invention also provides a method for synthesizing the compound above which comprises:

(a) contacting a starting compound having the structure:

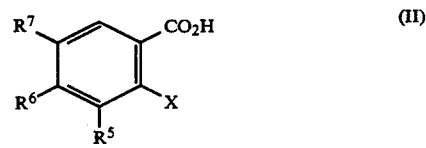

(II)

or

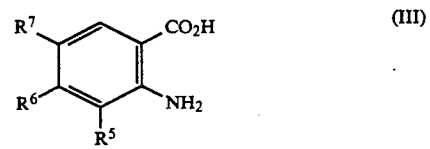

(III)

wherein $R^5$, $R^6$, and $R^7$ are the same or different and are hydrogen, a saturated or unsaturated alkyl group having 1 to 5 carbon atoms, sulfate, phosphate, a hydroxy group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-acyl group, an O-aroyl group, an O-aryl group, a nitro group, an amino group, an N-alkylamino group having 1 to 5 carbon atoms, an N,N-dialkylamino group with each alkyl having 1 to 5 carbon atoms, an aminoalkyloxy group having 1 to 5 carbon atoms, an N-alkyl-aminoalkyloxy group wherein each alkyl is the same or different having 1 to 5 carbon atoms, an N,N-dialkyl-aminoalkyloxy group wherein each alkyl is the same or different having 1 to 5 carbon atoms, a quaternary ammonium alkyloxy salt, or a halogen; and X is a halogen;

with a compound having the structure:

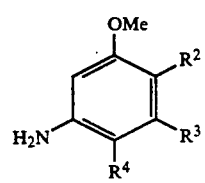
(IV)

or

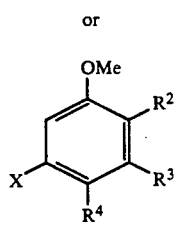
(V)

respectively, wherein $R^2$ and $R^3$ are the same or different and are hydrogen, a saturated or unsaturated alkyl group having to 5 carbon atoms, a hydroxy group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-acyl group, an O-aroyl group, or an O-aryl group;

$R^4$ is hydrogen, a saturated or unsaturated alkyl group having 1 to 5 carbon atoms, a hydroxy group, a hydroxymethyl group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-alkyloxyalkyloxyalkyl group wherein each alkyl is the same or different having 1 to 5 carbon atoms, an O-acyl group, an O-aroyl group, or an O-aryl group; and X is a halogen or a nitro group;

under such conditions so as to form a compound having the structure:

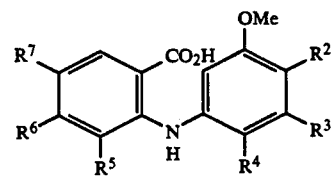
(VI)

wherein $R^2$, $R^3$, $R^4$, $R^5$, $R^6$, and $R^7$ are the same as defined previously;

(b) treating the compound formed in step (a) under such conditions so as to form a compound having the structure:

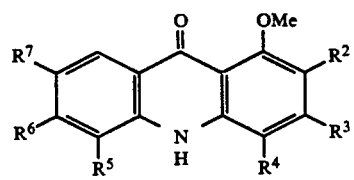
(VII)

wherein $R^2$, $R^3$, $R^4$, $R^5$, $R^6$, and $R^7$ are the same as defined previously;

(c) treating the compound formed in step (b) under such conditions so as to form a compound having the structure:

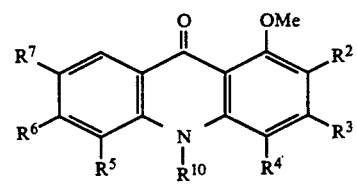
(VIII)

wherein $R^2$, $R^3$, $R^4$, $R^5$, $R^6$, and $R^7$ are the same as defined previously; and $R^{10}$ is hydrogen, a saturated or unsaturated alkyl group having 1 to 5 carbon atoms, an aminoalkyl group having 1 to 5 carbon atoms, an N-alkylaminoalkyl group wherein each alkyl is the same or different having 1 to 5 carbon atoms, an N,N-dialkylaminoalkyl group wherein each alkyl is the same or different having 1 to 5 carbon atoms, or an amino acid moiety; and (d) treating the compound formed in step (c) under such conditions so as to form a compound having the structure:

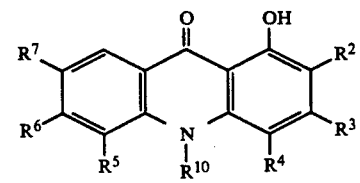
(I)

wherein $R^2$, $R^3$, $R^4$, $R^5$, $R^6$, $R^7$, and $R^{10}$ are the same as defined previously.

The present invention also provides a compound having the structure:

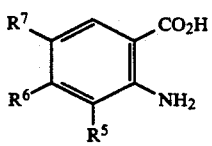 (III)

wherein $R^5$, $R^6$, and $R^7$ are the same or different and are hydrogen, a saturated or unsaturated alkyl group having 1 to 5 carbon atoms, sulfate, phosphate, a hydroxy group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-acyl group, an O-aroyl group, an O-aryl group, a nitro group, an amino group, an N-alkylamino group having 1 to 5 carbon atoms, an N,N-dialkylamino group with each alkyl having 1 to 5 carbon atoms, an aminoalkyloxy group having 1 to 5 carbon atoms, an N-alkyl-aminoalkyloxy group wherein each alkyl is the same or different having 1 to 5 carbon atoms, an N,N-dialkyl-aminoalkyloxy group wherein each alkyl is the same or different having 1 to 5 carbon atoms, a quaternary ammonium alkyloxy salt, or a halogen;

The present invention also provides a compound having the structure:

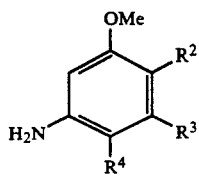 (IV)

or

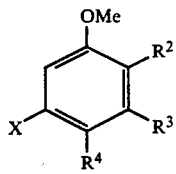 (V)

wherein
$R^2$ and $R^3$ are the same or different and are hydrogen, a saturated or unsaturated alkyl group having 1 to 5 carbon atoms, a hydroxy group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-acyl group, an O-aroyl group, or an O-aryl group;
$R^4$ is hydrogen, a saturated or unsaturated alkyl group having 1 to 5 carbon atoms, a hydroxy group, a hydroxymethyl group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having to 5 carbon atoms, an O-alkyloxyalkyloxyalkyl group wherein each alkyl is the same or different having 1 to 5 carbon atoms, an O-acyl group, an O-aroyl group, or an O-aryl group; and
X is a halogen or a nitro group.

The present invention further provides a compound having the structure:

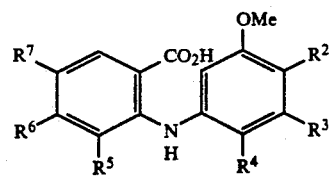 (VI)

wherein $R^2$ and $R^3$ are the same or different and are hydrogen, a saturated or unsaturated alkyl group having 1 to 5 carbon atoms, a hydroxy group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-acyl group, an O-aroyl group, or an O-aryl group;
$R^4$ is hydrogen, a saturated or unsaturated alkyl group having 1 to 5 carbon atoms, a hydroxy group, a hydroxymethyl group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-alkyloxyalkyloxyalkyl group wherein each alkyl is the same or different having 1 to 5 carbon atoms, an O-acyl group, an O-aroyl group, or an O-aryl group;
$R^5$, $R^6$, and $R^7$ are the same or different and are hydrogen, a saturated or unsaturated alkyl group having 1 to 5 carbon atoms, sulfate, phosphate, a hydroxy group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-acyl group, an O-aroyl group, an O-aryl group, a nitro group, an amino group, an N-alkylamino group having 1 to 5 carbon atoms, an N,N-dialkylamino group with each alkyl having 1 to 5 carbon atoms, an aminoalkyloxy group having 1 to 5 carbon atoms, an N-alkyl-aminoalkyloxy group wherein each alkyl is the same or different having 1 to 5 carbon atoms, an N,N-dialkyl-aminoalkyloxy group wherein each alkyl is the same or different having to 5 carbon atoms, a quaternary ammonium alkyloxy salt, or a halogen.

The present invention further provides a compound having the structure:

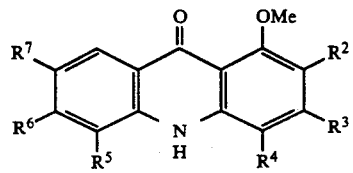 (VII)

wherein
$R^2$ and $R^3$ are the same or different and are hydrogen, a saturated or unsaturated alkyl group having 1 to 5 carbon atoms, a hydroxy group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-acyl group, an O-aroyl group, or an O-aryl group;

$R^4$ is hydrogen, a saturated or unsaturated alkyl group having 1 to 5 carbon atoms, a hydroxy group, a hydroxymethyl group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having to 5 carbon atoms, an O-alkyloxyalkyloxyalkyl group wherein each alkyl is the same or different having 1 to 5 carbon atoms, an O-acyl group, an O-aroyl group, or an O-aryl group;

$R^5$, $R^6$, and $R^7$ are the same or different and are hydrogen, a saturated or unsaturated alkyl group having 1 to 5 carbon atoms, sulfate, phosphate, a hydroxy group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-acyl group, an O-aroyl group, an O-aryl group, a nitro group, an amino group, an N-alkylamino group having 1 to 5 carbon atoms, an N,N-dialkylamino group with each alkyl having 1 to 5 carbon atoms, an aminoalkyloxy group having 1 to 5 carbon atoms, an N-alkyl-aminoalkyloxy group wherein each alkyl is the same or different having 1 to 5 carbon atoms, an N,N-dialkyl-aminoalkyloxy group wherein each alkyl is the same or different having 1 to 5 carbon atoms, a quaternary ammonium alkyloxy salt, or a halogen.

The present invention still further provides a compound having the structure:

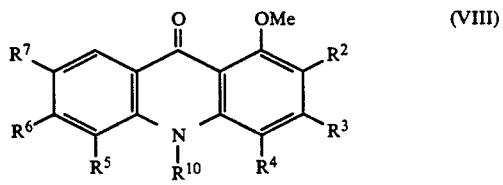

wherein $R^2$ and $R^3$ are the same or different and are hydrogen, a saturated or unsaturated alkyl group having 1 to 5 carbon atoms, a hydroxy group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-acyl group, an O-aroyl group, or an O-aryl group;

$R^4$ is hydrogen, a saturated or unsaturated alkyl group having 1 to 5 carbon atoms, a hydroxy group, a hydroxymethyl group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having to 5 carbon atoms, an O-alkyloxyalkyloxyalkyl group wherein each alkyl is the same or different having 1 to 5 carbon atoms, an O-acyl group, an O-aroyl group, or an O-aryl group;

$R^5$, $R^6$, and $R^7$ are the same or different and are hydrogen, a saturated or unsaturated alkyl group having 1 to 5 carbon atoms, sulfate, phosphate, a hydroxy group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-acyl group, an O-aroyl group, an O-aryl group, a nitro group, an amino group, an N-alkylamino group having 1 to 5 carbon atoms, an N,N-dialkylamino group with each alkyl having 1 to 5 carbon atoms, an aminoalkyloxy group having 1 to 5 carbon atoms, an N-alkyl-aminoalkyloxy group wherein each alkyl is the same or different having 1 to 5 carbon atoms, an N,N-dialkyl-aminoalkyloxy group wherein each alkyl is the same or different having to 5 carbon atoms, a quaternary ammonium alkyloxy salt, or a halogen; and $R^{10}$ is hydrogen, a saturated or unsaturated alkyl group having 1 to 5 carbon atoms, an aminoalkyl group having 1 to carbon atoms, an N-alkylaminoalkyl group wherein each alkyl is the same or different having 1 to 5 carbon atoms, an N,N-dialkylaminoalkyl group wherein each alkyl is the same or different having 1 to 5 carbon atoms, or an amino acid moiety.

The present invention also provides a pharmaceutical composition which comprises an amount of a compound of any of formulas I, III, IV, V, VI, VII, or VIII and a pharmaceutically acceptable carrier.

Lastly, the present invention provides a method of inhibiting growth of tumor cells which comprises contacting the tumor cells with an effective amount of a compound of any of formulas I, III, IV, V, VI, VII, or VIII, effective to inhibit growth of tumor cells.

DETAILED DESCRIPTION OF THE INVENTION

The present invention provides a compound having the structure:

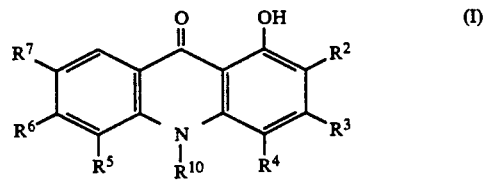

wherein $R^2$ and $R^3$ are the same or different and are hydrogen, a saturated or unsaturated alkyl group having 1 to 5 carbon atoms, a hydroxy group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-acyl group, an O-aroyl group, or an O-aryl group;

$R^4$ is hydrogen, a saturated or unsaturated alkyl group having 1 to 5 carbon atoms, a hydroxy group, a hydroxymethyl group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-alkyloxyalkyloxyalkyl group wherein each alkyl is the same or different having 1 to 5 carbon atoms, an O-acyl group, an O-aroyl group, or an O-aryl group;

$R^5$, $R^6$, and $R^7$ are the same or different and are hydrogen, a saturated or unsaturated alkyl group having 1 to 5 carbon atoms, sulfate, phosphate, a hydroxy group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-acyl group, an O-aroyl group, an O-aryl group, a nitro group, an amino group, an N-alkylamino group having 1 to 5 carbon atoms, an N,N-dialkylamino group with each alkyl having 1 to 5 carbon atoms, an aminoalkyloxy group having 1 to 5 carbon atoms, an N-alkyl-aminoalkyloxy group wherein each alkyl is the same or different having 1 to 5 carbon atoms, an N,N-dialkyl-aminoalkyloxy group wherein each alkyl is the same or different having 1 to 5 carbon atoms, a quaternary ammonium alkyloxy salt, or a halogen; and $R^{10}$ is hydrogen, a saturated or unsaturated alkyl group having 1 to 5 carbon atoms, an aminoalkyl group having 1 to 5 carbon atoms, an N-alkylaminoalkyl group wherein each alkyl is the same or different having 1 to 5 carbon atoms, an N,N-dialkylaminoalkyl group wherein each alkyl is the same or different having 1 to 5 carbon atoms, or an amino acid moiety.

In the preferred embodiment, $R^2$ and $R^3$ are the same or different and are hydrogen, a methyl group, an ethyl group, an allyl group, a phenyl group, a hydroxy group, a methoxy group, an ethoxy group, an alloxy group, a phenoxy group, an O-methoxymethyl group, an O-benzyloxymethyl group, an O-acetyl group, an O-benzoyl group, or an O-benzyl group.

In the preferred embodiment, $R^4$ is hydrogen, a methyl group, an ethyl group, an allyl group, a phenyl group, a hydroxy group, a hydroxymethyl group, a methoxy group, an ethoxy group, an alloxy group, a phenoxy group, an O-methoxymethyl group, an O-benzyloxymethyl group, an O-methoxymethoxymethyl group, an O-acetyl group, an O-benzoyl group, or an O-benzyl group.

In the preferred embodiment, $R^5$, $R^6$, and $R^7$ are the same or different and are hydrogen, a methyl group, an ethyl group, an allyl group, a phenyl group, a sulfate, a phosphate, a hydroxy group, a methoxy group, an ethoxy group, an alloxy group, a phenoxy group, an O-methoxymethyl group, an O-benzyloxymethyl group, an O-acetyl group, an O-benzoyl group, an O-benzyl group, a nitro group, an amino group, a methylamino group, a diethylamino group, an aminoethyloxy group, an N-methyl-aminopropyloxy group, an N,N-diethylaminoethyloxy group, an N,N-dihydroxyethyl-N-methylammonium ethyloxy chloride, a fluorine, a chlorine, a bromine or an iodine.

In the preferred embodiment, $R^{10}$ is hydrogen, a methyl group, an ethyl group, an allyl group, a phenyl group, an aminoethyl group, an N-methylaminoethyl group, an N,N-dimethylaminopropyl group, an N,N-diethylaminoethyl group, or an L-alanine.

In the most preferred embodiment, $R^2$, $R^3$, $R^4$, and $R^5$ are methoxy groups, $R^6$ is a hydroxy group, and $R^{10}$ is a methyl group.

Compounds having the above-identified structure, although not limited to the following compounds, may be selected from the group consisting of:

6-benzyloxy-1-hydroxy-10-methyl-2,3,4,5-tetramethoxy-9 acridone,
5-benzyloxy-1-hydroxy-10-methyl-2,3,4-trimethoxy-9-acridone,
6-benzyloxy-1-hydroxy-10-methyl-2,3,4-trimethoxy-9-acridone,
7-benzyloxy-1-hydroxy-10-methyl-2,3,4-trimethoxy-9-acridone,
5-benzyloxy-1-hydroxy-10-methyl-2,3,4,6-tetramethoxy-9 acridone,
6-nitro-10-methyl-2,3,4-trimethoxy-9-acridone,
6-nitro-10-methoxy-2,3,4-trimethoxy-acridone,
1,6-dihydroxy-2,3,4,5-tetramethoxy-9-acridone,
1,6-dihydroxy-2,3,4,5-tetramethoxy-10-methyl-9 acridone,
1,5-dihydroxy-10-methyl-2,3,4-trimethoxy-9-acridone,
1,6-dihydroxy-10-methyl-2,3,4-trimethoxy-9-acridone,
1,7-dihydroxy-10-methyl-2,3,4-trimethoxy-9-acridone,
1,5-dihydroxy-10-methyl-2,3,4,6-tetramethoxy-9acridone, or
2-amino-3-(1,6-dihydroxy-2,3,4,5-tetramethoxy-9-acridone-1-yl)propionic acid.

The present invention also provides a method for synthesizing the compound of formula I which comprises:

(a) contacting a starting compound having the structure:

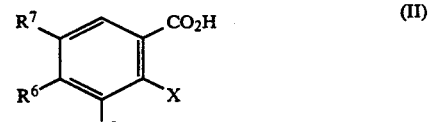

(II)

or

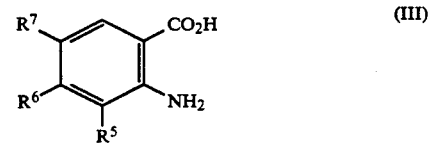

(III)

wherein $R^5$, $R^6$, and $R^7$ are the same or different and are hydrogen, a saturated or unsaturated alkyl group having 1 to 5 carbon atoms, sulfate, phosphate, a hydroxy group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having to 5 carbon atoms, an O-acyl group, an O-aroyl group, an O-aryl group, a nitro group, an amino group, an N-alkylamino group having 1 to 5 carbon atoms, an N,N-dialkylamino group with each alkyl having 1 to 5 carbon atoms, an aminoalkyloxy group having 1 to 5 carbon atoms, an N-alkyl-aminoalkyloxy group wherein each alkyl is the same or different having 1 to 5 carbon atoms, an N,N-dialkyl-aminoalkyloxy group wherein each alkyl is the same or different having 1 to 5 carbon atoms, a quaternary ammonium alkyloxy salt, or a halogen; and X is a halogen;

with a compound having the structure:

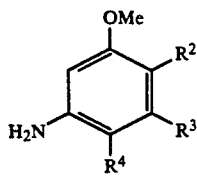

(IV)

or

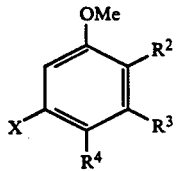

(V)

respectively, wherein $R^2$ and $R^3$ are the same or different and are hydrogen, a saturated or unsaturated alkyl group having to 5 carbon atoms, a hydroxy group, a saturated or unsaturated alkyloxy group having 1 to 5 carbon atoms, an O-alkyloxyalkyl group wherein each alkyl is the same or different having to 5 carbon atoms, an O-aryloxyalkyl group with the alkyl having 1 to 5 carbon atoms, an O-acyl group, an O-aroyl group, or an O-aryl group;

$R^4$ is hydrogen, a saturated or unsaturated alkyl group having 1 to 5 carbon atoms, a hydroxy group, a hydroxymethyl group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-alkyloxyalkyloxyalkyl group wherein each alkyl is the same or different having 1 to 5 carbon atoms, an O-acyl group, an O-aroyl group, or an O-aryl group; and X is a halogen or a nitro group;

under such conditions so as to form a compound having the structure:

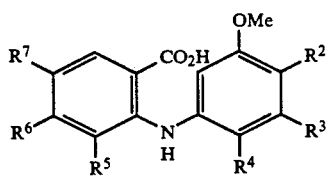

(VI)

wherein $R^2$, $R^3$, $R^4$, $R^5$, $R^6$, and $R^7$ are the same as defined previously;

(b) treating the compound formed in step (a) under such conditions so as to form a compound having the structure:

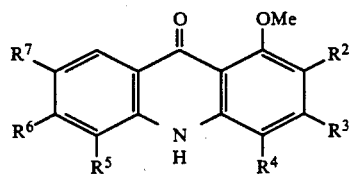

(VII)

wherein $R^2$, $R^3$, $R^4$, $R^5$, $R^6$, and $R^7$ are the same as defined previously;

(c) treating the compound formed in step (b) under such conditions so as to form a compound having the structure:

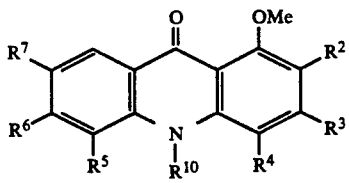

(VIII)

wherein $R^2$, $R^3$, $R^4$, $R^5$, $R^6$, and $R^7$ are the same as defined previously; and $R^{10}$ is hydrogen, a saturated or unsaturated alkyl group having 1 to 5 carbon atoms, an aminoalkyl group having to 5 carbon atoms, an N-alkylaminoalkyl group wherein each alkyl is the same or different having 1 to 5 carbon atoms, an N,N-dialkylaminoalkyl group wherein each alkyl is the same or different having 1 to 5 carbon atoms, or an amino acid moiety; and (d) treating the compound formed in step (c) under such conditions so as to form a compound having the structure:

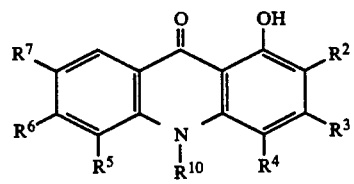

(I)

wherein $R^2$, $R^3$, $R^4$, $R^5$, $R^6$, $R^7$, and $R^{10}$ are the same as defined previously.

The compounds of formula II, III, IV, and V are prepared as follows. The compounds of formula II are prepared using starting materials and procedures known to those skilled in the art. For example, 2-chloro-4-nitrobenzoic acid and 2-chloro-5-nitrobenzoic acid are listed in Aldrich, Catalog Handbook of Fine Chemicals. The compounds of formula III are prepared from the known 2-nitrobenzoic acids. For example, vanillin is converted into 4-benzyloxy-3-methoxy-2-nitrobenzoic acid (Hey, D. H. and Lobo, L. C., *J. Chem. Soc.* 1954; 2246). The compounds of formula IV and Formula V wherein $R^4$ is methyl, O-protected hydroxymethyl, alkyloxy or benzyloxy are synthesized from known benzaldehyde derivatives. For example, treatment of 2,3,4-trimethoxybenzaldehyde with fuming nitric acid gives 2-nitro-4,5,6-trimethoxybenzaldehyde (Budesinsky et al., *Coll. Czech. Chem. Comm.* 1976; 41: 3045), which is then converted into 2,3,4,5-tri-methoxyaniline via Baeyer-Villiger reaction (Baeyer, Villiger, *Chem Ber.* 1900; 33: 8580; Goafrey et al., *J. Chem. Soc. Perkin 1* 1974; 1353), followed by O-methylation, and reduction of the nitro function. The compounds of Formula IV are converted into the corresponding halobenzenes of Formula V via Sandmeyer reaction.

The compounds of formula IV and V, wherein $R^4$ is methyl, hydroxymethyl or it O-protected congeners, are synthesized from the above 2-nitrobezaldehyde. The aldehyde function is first reduced to methyl or hydroxymethyl group. The hydroxy function of the hydroxymethyl is then protected by treatment with O-protecting agents such as chloromethyl methyl ether, benzylchloride and the like. The nitro group is then reduced to the corresponding aniline (formula IV) and halobenzene (formula V) derivatives. By following the same procedure, compounds of formula IV and V are prepared from various 4-methoxybenzaldehyde derivatives.

The contacting in step (a) comprises the Ullmann condensation of 2-halobenzoic acid compounds of formula II with aniline compounds of formula IV, or the condensation of anthranilic acid compounds of formula III with halobenzene compounds of formula V to give diphenylamine carbonic acid compounds of formula VI (Hughes, et al., *Aust. J. Sci.,* 1950; A3: 497).

In the preferred embodiment, the contacting in step (a) is performed in a mixture of copper with or without copper(I) oxide ($Cu_2O$), potassium carbonate, in a solvent with a boiling point above 110° C., at a temperature range of 100° C. to 200° C. for a period of 1 hour to 2 days. The solvent is an alcohol such as n-butanol, heptanol, hexanol and the like, or an ether such as diglyme, phenylether and the like. Preferably, the contacting is carried out at a temperature range of 120° C. to 170° C.

The molar ratio of the reactants in step (a) of compounds of formula II to compounds of formula IV or of compounds of formula III to compounds of formula V can be 1 to 5, but is preferably 1 to 1.5.

Upon completion of the reaction in step (a), the mixture is cooled and the solvent is removed by evaporation in vacuo or by steam distillation. The residue is triturated with diluted alkali solution such as sodium hydroxide, potassium hydroxide, ammonium hydroxide and the like, or with saturated aqueous solution of metal carbonate or bicarbonate such as sodium (or potassium) carbonate or sodium (or potassium) bicarbonate and the like. The mixture is filtered, washed with water, and the combined filtrate and the washings are acidified with diluted acid such as hydrochloric acid, sulfuric acid, or acetic acid and the like. When the product is precipitated out, the product is collected by filtration, followed by purification by either recrystallization or liquid chromatography. If no precipitated product appears in the solution after acidified, the mixture is filtered and then extracted with organic solvent such as chloroform, ethyl acetate, or ether. The product of compound of formula VI is obtained by crystallization or chromatography.

The treating in step (b) comprises the cyclization of the compounds of formula VI to give the multisubstituted 1-methoxy-9-acridone compounds of formula VII.

In one embodiment, the treating in step (b) comprises contacting the compound formed in step (a) with an inorganic acid such as sulfuric acid or polyphosphoric acid at temperature range of 60° C. to 100° C. for a period of 20 minutes to 5 hours.

In another embodiment, the treating in step (b) comprises contacting the compound formed in step (a) with phosphoryl chloride followed by acid hydrolysis, or by modification of a procedure developed by Cain et al. (Cain et al., *J. Med. Chem* 1975; 18: 1110). For example, the Compound formed in step (b) is treated with thionyl chloride and pyridine in chloroform for 15 minutes to 2 hours, preferably from 15 to 30 minutes. The reaction mixture is then evaporated to dryness in vacuo and the residue is treated with piperidine and triethylamine to form the piperidide derivative which is not isolated but is directly cyclized by treatment with phosphonyl chloride followed by hydrolysis with diluted hydrochloric acid to give the compound of formula VII.

The treating in step (c) comprises the N-alkylation of the compounds of formula VII to give the N-alkylated compounds of formula VIII.

In the preferred embodiment, the treating in step (c) comprises contacting the compound formed in step (b) with an alkylhalide such as methyl iodide, ethyl iodide, and the like, in a mixture of base such as potassium carbonate in acetone, potassium carbonate in dimethylformamide, or sodium hydride in dimethylformamide. Preferably, the base is potassium carbonate in acetone.

The contacting in step (d) comprises the de-O-methylation of the compounds of formula VIII to give the multisubstituted 1-hydroxy-9-acridone compounds of formula I.

In the preferred embodiment, the treating in step (d) comprises contacting the compound formed in step (c) with an acid such as hydrochloric acid, hydrobromic acid, sulfuric acid, or phosphoric acid, in an alcohol, or a boron trihalide such as boron trifluoride, boron trichloride, or boron tribromide, in an ethereal solution at temperature range of 40 to 140 ° C. for 0.5 hours to 2 days. Preferably, the treating in step (d) is performed in hydrochloric acid in alcohol such as methanol, ethanol, or propanol alcohol and preferably methanol or ethanol alcohol (Crow, W. D. and Price, J. R., *Aust. J. Sci.* 1949; A2: 225).

The compounds of formula I with O-benzyloxy function(s) at the 2, 3, 4, 5, 6, and 7 position(s) of the acridone nucleus are de-O-benzylated by catalytic hydrogenation to give the free hydroxy 1-hydroxy-9-acridone congeners. The compounds of formula I bearing a nitro substituent at the C-6 and C-7 positions are reduced to amino function by treatment with sodium or potassium bisulfite or other reducing agents, or by catalytic hydrogenation. The resulting amino 9-acridones are then converted into secondary, tartial amine by treatment with alkylhalide such as methyl iodide, ethyl iodide and the like. The amino group of 9-acridones are also converted into their corresponding azido derivatives. The 9-acridones of formula I containing an amino group at the C-6 or C-7 positions are converted into C-6 or C-7 halo acridone compounds via Sandmeyer reaction. The compounds of formula I with a O-protected hydroxymethyl function at the C-4 position are treated with inorganic acid in alcohol such as hydrochloric acid in methanol and the like, or treated with boron trihalide as defined previously. The synthesized 4-hydroxymethyl-1-hydroxy-9-acridones of formula I are converted into their N-alkylcarbamates by a known procedure (Archer et al., *J. Med. Chem.* 1988; 31: 254–360).

The present invention also provides a compound having the structure:

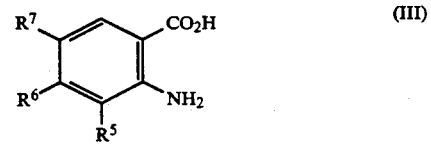

(III)

wherein $R^5$, $R^6$, and $R^7$ are the same or different and are hydrogen, a saturated or unsaturated alkyl group having 1 to 5 carbon atoms, sulfate, phosphate, a hydroxy group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-acyl group, an O-aroyl group, an O-aryl group, a nitro group, an amino group, an N-alkylamino group having 1 to 5 carbon atoms, an N,N-dialkylamino group with each alkyl having 1 to 5 carbon atoms, an aminoalkyloxy group having 1 to 5 carbon atoms, an N-alkyl-aminoalkyloxy group wherein each alkyl is the same or different having 1 to 5 carbon atoms, an N,N-dialkyl-aminoalkyloxy group wherein each alkyl is the same or different having 1 to 5 carbon atoms, a quaternary ammonium alkyloxy salt, or a halogen.

Compounds having the above-identified structure, although not limited to the following compounds, may be selected from the group consisting of:
  4-benzyloxy-3-methoxyanthranilic acid,
  3-benzyloxyanthranilic acid,
  3-methoxymethoxyanthranilic acid,
  3-methoxyanthranilic acid,
  5-benzyloxyanthranilic acid,
  5-methoxymethoxyanthranilic acid,
  5-methoxyanthranilic acid,
  4-methoxymethoxy-3-methoxyanthranilic acid, or
  3,4-dimethoxyanthranilic acid.

The present invention also provides a compound having the structure:

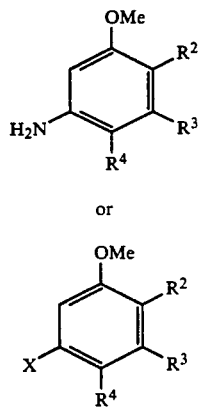

wherein
  $R^2$ and $R^3$ are the same or different and are hydrogen, a saturated or unsaturated alkyl group having 1 to 5 carbon atoms, a hydroxy group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-acyl group, an O-aroyl group, or an O-aryl group;
  $R^4$ is hydrogen, a saturated or unsaturated alkyl group having 1 to 5 carbon atoms, a hydroxy group, a hydroxymethyl group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-alkyloxyalkyloxyalkyl group wherein each alkyl is the same or different having 1 to 5 carbon atoms, an O-acyl group, an O-aroyl group, or an O-aryl group; and
  X is a halogen or a nitro group.

Compounds having the above-identified structure, although not limited to the following compounds, may be selected from the group consisting of:
  2-hydroxy-1-nitro-3,4,5-trimethoxybenzene,
  2-hydroxy-1-nitro-3,4,6-trimethoxybenzene,
  2-hydroxy-1-nitro-3,5,6-trimethoxybenzene,
  1-nitro-2,3,4,5-tetramethoxybenzene,
  1-nitro-2,3,4,6-tetramethoxybenzene,
  1-nitro-2,4,5,6-tetramethoxybenzene,
  2-hydroxymethyl-1-nitro-3,4,5-trimethoxybenzene,
  3,5-dimethoxy-2-hydroxymethyl-1-nitrobenzene,
  4,5-dimethoxy-2-hydroxymethyl-1-nitrobenzene,
  2-methoxymethoxymethyl-1-nitro-3,4,5trimethoxybenzene,
  2-benzyloxymethyl-1-nitro-3,4,5-trimethoxybenzene,
  2-benzyloxymethyl-3,5-dimethoxy-1-nitrobenzene,
  2-benzyloxymethyl-4,5-dimethoxy-1-nitrobenzene,
  3,5-dimethoxy-2-methoxymethoxymethyl-1-nitrobenzene,
  4,5-dimethoxy-2-methoxymethoxymethyl-1-nitrobenzene,
  1-chloro-2-methoxymethoxymethyl-3,4,5trimethoxybenzene,
  1-chloro-2-benzyloxymethyl-3,4,5-trimethoxybenzene,
  1-chloro-2-methoxymethoxymethyl-3,5-dimethoxybenzene,
  1-chloro-2-benzyloxymethyl-3,5-dimethoxybenzene,
  1-chloro-2-benzyloxymethyl-5-methoxybenzene,
  1-chloro-2-methyl-3,4,5-trimethoxybenzene,
  1-chloro-2-methyl-4,5-dimethoxybenzene,
  1-bromo-2-methoxymethoxymethyl-3,4,5-trimethoxybenzene,
  1-bromo-2-benzyloxymethyl-3,4,5-trimethoxybenzene,
  1-bromo-2-methoxymethoxymethyl-3,5-dimethoxybenzene,
  1-bromo-2-benzyloxymethyl-3,5-dimethoxybenzene,
  1-bromo-2-benzyloxymethyl-5-methoxybenzene,
  1-bromo-2-methyl-3,4,5-trimethoxybenzene,
  1-bromo-2-methyl-4,5-dimethoxybenzene,
  1-iodo-2-methoxymethoxymethyl-3,4,5-trimethoxybenzene,
  1-iodo-2-benzyloxymethyl-3,4,5-trimethoxybenzene,
  1-iodo-2-methoxymethoxymethyl-3,5-dimethoxybenzene,
  1-iodo-2-benzyloxymethyl-3,5-dimethoxybenzene,
  1-iodo-2-benzyloxymethyl-5-methoxybenzene,
  1-iodo-2-methyl-3,4,5-trimethoxybenzene,
  1-iodo-2-methyl-4,5-dimethoxybenzene,
  2,3,4,5-tetramethoxyaniline,
  2,3,5-trimethoxyaniline,
  2,4,5-trimethoxyaniline,
  2,3,4,6-tetramethoxyaniline,
  2,3,5,6-tetramethoxyaniline,
  2-methoxymethoxymethyl-3,4,5-trimethoxyaniline,
  2-benzyloxymethyl-3,4,5-trimethoxyaniline,
  2-methoxymethoxymethyl-3,5-dimethoxyaniline,
  2-benzyloxymethoxymethyl-4,5-dimethoxyaniline,
  2-methyl-3,4,5-trimethoxyaniline,
  3,5-dimethoxy-2-methylaniline, or
  4,5-dimethoxy-2-methylaniline.

The present invention also provides a compound having the structure:

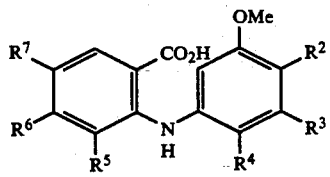

(VI)

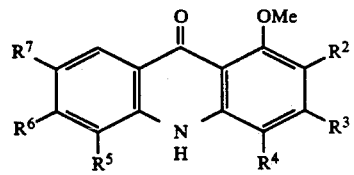

(VII)

wherein
$R^2$ and $R^3$ are the same or different and are hydrogen, a saturated or unsaturated alkyl group having 1 to 5 carbon atoms, a hydroxy group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-acyl group, an O-aroyl group, or an O-aryl group;

$R^4$ is hydrogen, a saturated or unsaturated alkyl group having 1 to 5 carbon atoms, a hydroxy group, a hydroxymethyl group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-alkyloxyalkyloxyalkyl group wherein each alkyl is the same or different having 1 to 5 carbon atoms, an O-acyl group, an O-aroyl group, or an O-aryl group; and $R^5$, $R^6$, and $R^7$ are the same or different and are hydrogen, a saturated or unsaturated alkyl group having 1 to 5 carbon atoms, sulfate, phosphate, a hydroxy group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-acyl group, an O-aroyl group, an O-aryl group, a nitro group, an amino group, an N-alkylamino group having 1 to 5 carbon atoms, an N,N-dialkylamino group with each alkyl having 1 to 5 carbon atoms, an aminoalkyloxy group having 1 to 5 carbon atoms, an N-alkyl-aminoalkyloxy group wherein each alkyl is the same or different having 1 to 5 carbon atoms, an N,N-dialkyl-aminoalkyloxy group wherein each alkyl is the same or different having to 5 carbon atoms, a quaternary ammonium alkyloxy salt, or a halogen.

Compounds having the above-identified structure, although not limited to the following compounds, may be selected from the group consisting of:
4-benzyloxy-3-methoxy-N-(2,3,4,5-tetramethoxyphenyl) anthranilic acid,
3-benzyloxy-N-(2,3,4,5-tetramethoxyphenyl)anthranilicacid,
4-nitro-N-(2,3,4,5-tetramethoxyphenyl)anthranilic acid, or
4-benzyloxy-3-methoxy-N-(2-methoxymethoxymethyl-3,4,5-trimethoxyphenyl)anthranilic acid.

The present invention further provides a compound having the structure:

herein
$R^2$ and $R^3$ are the same or different and are hydrogen, a saturated or unsaturated alkyl group having 1 to 5 carbon atoms, a hydroxy group, a saturated or unsaturated alkyloxy group having to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-acyl group, an O-aroyl group, or an O-aryl group;

$R^4$ is hydrogen, a saturated or unsaturated alkyl group having 1 to 5 carbon atoms, a hydroxy group, a hydroxymethyl group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-alkyloxyalkyloxyalkyl group wherein each alkyl is the same or different having 1 to 5 carbon atoms, an O-acyl group, an O-aroyl group, or an O-aryl group; and $R^5$, $R^6$, and $R^7$ are the same or different and are hydrogen, a saturated or unsaturated alkyl group having 1 to 5 carbon atoms, sulfate, phosphate, a hydroxy group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-acyl group, an O-aroyl group, an O-aryl group, a nitro group, an amino group, an N-alkylamino group having 1 to 5 carbon atoms, an N,N-dialkylamino group with each alkyl having 1 to 5 carbon atoms, an aminoalkyloxy group having 1 to 5 carbon atoms, an N-alkyl-aminoalkyloxy group wherein each alkyl is the same or different having 1 to 5 carbon atoms, an N,N-dialkyl-aminoalkyloxy group wherein each alkyl is the same or different having 1 to 5 carbon atoms, a quaternary ammonium alkyloxy salt, or a halogen.

Compounds having the above-identified structure, although not limited to the following compounds, may be selected from the group consisting of:
6-benzyloxy-1,2,3,4,5-pentamethoxy-9-acridone,
5-benzyloxy-1,2,3,4-tetramethoxy-9-acridone,
6-nitro-1,2,3,4-tetramethoxy-9-acridone, or
6-benzyloxy-1,2,3,5-tetramethoxy-4-methoxymethoxymethyl-9-acridone.

The present invention further provides a compound having the structure:

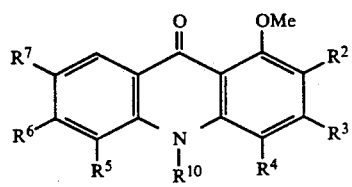

(VIII)

wherein
- R² and R³ are the same or different and are hydrogen, a saturated or unsaturated alkyl group having 1 to 5 carbon atoms, a hydroxy group, a saturated or unsaturated alkyloxy group having to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-acyl group, an O-aroyl group, or an O-aryl group;
- R⁴ is hydrogen, a saturated or unsaturated alkyl group having 1 to 5 carbon atoms, a hydroxy group, a hydroxymethyl group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having to 5 carbon atoms, an O-alkyloxyalkyloxyalkyl group wherein each alkyl is the same or different having 1 to 5 carbon atoms, an O-acyl group, an O-aroyl group, or an O-aryl group;
- R⁵, R⁶, and R⁷ are the same or different and are hydrogen, a saturated or unsaturated alkyl group having 1 to 5 carbon atoms, sulfate, phosphate, a hydroxy group, a saturated or unsaturated alkyloxy group having 1 to 5 carbon atoms, an O-alkyloxyalkyl group wherein each alkyl is the same or different having 1 to 5 carbon atoms, an O-aryloxyalkyl group with the alkyl having 1 to 5 carbon atoms, an O-acyl group, an O-aroyl group, an O-aryl group, a nitro group, an amino group, an N-alkylamino group having 1 to 5 carbon atoms, an N,N-dialkylamino group with each alkyl having 1 to 5 carbon atoms, an aminoalkyloxy group having 1 to 5 carbon atoms, an N-alkyl-aminoalkyloxy group wherein each alkyl is the same or different having 1 to 5 carbon atoms, an N,N-dialkyl-aminoalkyloxy group wherein each alkyl is the same or different having 1 to 5 carbon atoms, a quaternary ammonium alkyloxy salt, or a halogen; and
- R¹⁰ is hydrogen, a saturated or unsaturated alkyl group having 1 to 5 carbon atoms, an aminoalkyl group having 1 to 5 carbon atoms, an N-alkylaminoalkyl group wherein each alkyl is the same or different having 1 to 5 carbon atoms, an N,N-dialkylaminoalkyl group wherein each alkyl is the same or different having 1 to 5 carbon atoms, or an amino acid moiety.

Compounds having the above-identified structure, although not limited to the following compounds, may be selected from the group consisting of:
- 6-benzyloxy-10-methyl-1,2,3,4,5-pentamethoxy-9-acridone,
- 5-benzyloxy-10-methyl-1,2,3,4-tetramethoxy-9-acridone,
- 6-nitro-10-methyl-1,2,3,4-tetramethoxy-9-acridone, or
- 6-benzyloxy-4-methoxymethoxymethyl-10-methyl-1,2,3,5-tetramethoxy-9-acridone.

The present invention also provides a pharmaceutical composition which comprises an amount of a compound of any of formulas I, III, IV, V, VI, VII, or VIII and a pharmaceutically acceptable carrier. In the preferred embodiment, the amount is enough compound to effectively inhibit growth of tumor cells. More preferably, the amount is in a dose range of 5 to 200 mg./kg./day and most preferably, a dose range of 25 to 125 mg./kg./day.

The term "pharmaceutically acceptable carrier" encompasses any of the standard pharmaceutical carriers such as sterile solutions, tablets, coated tablets, and capsules. Typically, such carriers contain excipients such as starch, milk, sugar, certain types of clay, gelatin, steric acid, talc, vegetable fats or oils, gums, glycols, or other known excipients. Such carriers may also include flavor and color additives or other ingredients, such as compositions to increase solubility. Compositions to increase solubility include, but are not limited to, compounds which react with the hydrophobic regions of the subject compounds. Specifically, some examples of suitable agents include Emulphor (a polyoxylethylated fatty acid which is water miscible and non-toxic when diluted 1:10 with either sterile water or steril physiological saline solution) and polyvinylpyrrolidine. Compositions comprising such carriers are formulated by well known conventional methods.

The present invention also provides a method of inhibiting growth of tumor cells which comprises contacting the tumor cells with an effective amount of a compound of any of formulas I, III, IV, V, VI, VII, or VIII, effective to inhibit growth of tumor cells. The method may be performed both in vitro and in vivo. Preferably, the tumor cells are a lewis lung carcinoma, a mammary adenocarcinoma, or a melanoma.

When performed in vivo, the administration of the compound may be effected by any of the well known methods, including but not limited to oral, intravenous, intramuscular, and subcutaneous. The method of delivery, the amount to be delivered, and frequency of delivery, are expected to vary according to the situation, which carrier used, and result desired. However, those variables are readily determinable by one skilled in the art.

The following Experimental Details section and Examples are set forth to aid in an understanding of the invention. These sections are not intended to, and should not be construed to, limit in any way the invention set forth in the claims which follow thereafter.

EXPERIMENTAL DETAILS

Example 1

To a vigorously stirring suspension of 4-benzyloxy-3-methoxy-2-nitrobenzoic acid (10.918 g, 0.036 mol) in water (200 ml) containing sodium acetate trihydrate (4.5 g) was added portionwise of sodium hydrosulfite (31 g, 0.18 mol) for 2 hours at 70 °C. The reaction mixture was kept at this temperature for an additional 4 hours. After cooling, the precipitates were collected by filtration and washed with water. The product was recrystalized from ethanol to give 4-benzyloxy-3-methoxyanthranilic acid, 6.46 g (65.6%) with mp. 167-8 °C. 1H-NMR: Analyses: Calculated for $C_{15}H_{15}NO_4$: C, 65.92; H, 5.53; N, 5.13. Found: C, 66.14; H, 5.55; N, 5.24.

By following the same procedure, but using the corresponding 2-nitrobenzoic acids instead of 4-benzyloxy-3-methoxy-2-nitrobenzoic acid, the following corresponding anthranilic acid congeners (formula III) were obtained:
- 3-benzyloxyanthranilic acid,
- 3-methoxymethoxyanthranilic acid,
- 3-methoxyanthranilic acid,
- 5-benzyloxyanthranilic acid,
- 5-methoxymethoxyanthranilic acid,
- 5-methoxyanthranilic acid,
- 4-methoxymethoxy-3-methoxyanthranilic acid, and 3,4-dimethoxyanthranilic acid.

Example 2

A mixture of 2-nitro-4,5,6-trimethoxybenzaldehyde (19.3 g, 0.08 mol) and m-chloroperbenzoic acid (20.7 g, 0.12 mol) in chloroform (350 ml) was heated under reflux for 5 hours. After cooling, the reaction mixture was washed with 10% sodium bicarbonate solution and water. The solvent was removed by evaporation in vacuo and the residue was then treated with a mixture of 10% potassium hydroxide solution (potassium hydroxide 5.0 g, 0.088 mol in 50 ml of water) and methanol (150 ml) at room temperature under nitrogen. The solvent was removed in vacuo and the solid residue was dissolved in water (300 ml) and then acidified with 6N hydrochloric acid. The precipitated product was collected by filtration, washed well with water and dried to give (after recrystallization from 2-propanol) 13.1 g of 2-hydroxy-1-nitro-3,4,5-trimethoxybenzene, mp 72–73° C. $^1$H-NMR (CDCl$_3$): δ3.87, 3.94, and 4.08 (each 3H, s, 3×OMe), 7.32 (1H, s, H-6), 10.78 (1H, exchangeable, OH). Analyses: Calculated for C$_9$H$_{11}$NO$_6$: C, 47.16; H, 4.84; N, 6.11. Found: C, 47.11; H, 5.00; N, 6.17.

By following the same procedure, but using the corresponding benzaldehyde, the following compounds of formula IV were prepared:
2-hydroxy-1-nitro-3,4,6-trimethoxybenzene, and
2-hydroxy-1-nitro-3,5,6-trimethoxybenzene.

Example 3

1-Hydroxy-2-nitro-4,5,6-trimethoxybenzene (4.58 g, 0.02 mol) was treated with diazomethane (prepared from 1-methyl-3-nitro-1-nitrosoguanidine, 5.88 g, 0.04 mol) in ether (300 ml) for 4 hours at room temperature. The reaction mixture was evaporated in vacuo to dryness, and the residue was chromatographed on a silica gel column (3×40 cm) using hexane/ethyl acetate (9:1) as the eluent. 1-Nitro-2,3,4,5-tetramethoxybenzene was obtained as syrup, 3.45 g (71%). $^1$NMR (CDCl$_3$): δ3.80, 3.94, 3.96, and 3.98 (each 3H, s, 4×OMe), 7.18 (1H, s, H-6). Analyses: Calculated for C$_{10}$H$_{13}$NO$_6$: C, 49.38; H, 5.39; N, 5.76. Found: C, 49.14; H, 5.53; N, 5.75.

By following the same procedure, but using the corresponding benzaldehyde, the following compounds of formula IV were prepared:
1-nitro-2,3,4,6-tetramethoxybenzene, and
1-nitro-2,4,5,6-tetramethoxybenzene.

Example 4

A solution of 1-nitro-2,3,4,5-tetramethoxybenzene (1.22 g, 5 mmol) in ethanol (50 ml) was catalytically hydrogenated over 10% Pd/C (0.5 g) at 40 psi for 1 hour. After removal of the catalyst by filtration, the filtrate was evaporated in vacuo to dryness to give crude 2,3,4,5-tetramethoxyaniline. The pure product, 0.931 g (87%) with mp 99–100° C., was obtained by chromatography over a silica gel column (n-hexane/ethyl acetate, 4:1). 1H-NMR (CDCl$_3$): δ3.65 (2H, bs, NH$_2$), 3.78, 3.79, 3.80, 3.94 (each 3H, s, 4×MeO), 6.09 (1H, s, H6). Analyses: Calculated for C$_{10}$H$_{15}$NO$_4$C, 56.33; H, 7.09; N, 6.57. Found: C, 56.36; H, 7.04; N, 6.69.

By following the same procedure, but using the corresponding nitrobenzene, the following aniline congeners of formula IV were prepared.
2,3,5-trimethoxyaniline,
2,4,5-trimethoxyaniline,
2,3,4,6-tetramethoxyaniline, and
2,3,5,6-tetramethoxyaniline.

Example 5

Sodium borohydride (4.44 g. 0.12 mol) was added portionwise to a suspension of 2-nitro-4,5,6-trimethoxybenzaldehyde (24.2 g, 0.1 mol) in 200 ml during 0.5 hours at 5–10 ° C. in an ice-bath. The mixture was stirred for an additional 10 minutes, and the excess of NaBH$_4$ was destroyed by addition of acetic acid. The mixture was then concentrated in vacuo to dryness, and the solid residue was triturated with water. The solid was collected by filtration, washed with water and recrystallized from ethanol to give 22.1 g (90.9%) of 2-hydroxymethyl-1-nitro-3,4,5-trimethoxybenzene; mp 69–70° C. $^1$H-NMR (CDCl$_3$): δ2.89 (1H, b, exchangeable, OH) 3.94, 3.96, and 3.97 (each 3H, s, 3×OMe), 4.78 (2h, s, CH$_2$), 7.38 (1H, s, H-6). Analyses: Calculated for C$_{10}$H$_{13}$NO$_6$: C, 49.38; H, 5.39; N, 5.76. Found: C, 49.44; H, 5.43; N, 5.79.

By following the same procedure, but using the corresponding nitrobenzaldehyde, the following 2-hydroxymethyl-1-nitrobenzene derivatives were prepared:
3,5-dimethoxy-2-hydroxymethyl-1-nitrobenzene, and
4,5-dimethoxy-2-hydroxymethyl-1-nitrobenzene.

Example 6

To a mixture of 2-hydroxymethyl-1-nitro-3,4,5-trimethoxybenzene (6.5 g, 26.7 mmol) and N,N-diethylaniline (9.96 g, 66.8 mmol) in dry chloroform (150 ml) was added dropwise chloromethylmethyl ether (4.28 g, 53.5 mmol) in an ice-bath. After stirring at room temperature overnight, the reaction mixture was washed successively with 1% hydrochloric acid, water, 10% sodium bicarbonate solution and water, and dried over sodium sulfate. The solvent was removed by evaporation in vacuo and the residue was crystallized from hexane to give 7.62 g (99%) of 2-methoxymethoxymethyl-1-nitro-3,4,5-trimethoxybenzene, mp. 39–40 ° C. $^1$H-NMR (CDCl$_3$): δ3.40 (3H, s, CH$_2$OMe), 3.93 (6H, s, 2×OMe), 3.94 (3H, s, 1×OMe), 4.73 and 4.82 (each 2H, s, 2 ×CH2), 7.29 (1H, s, H-6). Analyses: Calculated for C$_{12}$H$_{17}$NO$_7$: C, 50.17; H, 5.59; N, 4.88. Found: C, 50.18; H, 5.92; N, 4.80.

By following the same procedure, but using the corresponding nitrobenzaldehyde, the following 2-hydroxymethyl-1-nitrobenzene derivatives were prepared:
2-benzyloxymethyl-1-nitro-3,4,5-trimethoxybenzene,
2-benzyloxymethyl-3,5-dimethoxy-1-nitrobenzene,
2-benzyloxymethyl-4,5-dimethoxy-1-nitrobenzene,
3,5-dimethoxy-2-methoxymethoxymethyl-1-nitrobenzene, and
4,5-dimethoxy-2-methoxymethoxymethyl-1-nitrobenzene.

Example 7

A solution of 2-methoxymethoxymethyl-1-nitro-3,4,5-trimethoxy-benzene (6.03 g, 21 mmol) in ethanol (150 ml) was catalytically hydrogenated over 5% palladium on carbon (3 g) at 50 psi for 2 hours. The catalyst was removed by filtration through a pad of Celite, and the filtered catalyst was washed with ethanol. The combined filtrate and the washings are concentrated in vacuo to dryness, and the product was purified by column chromatography (SiO$_2$, 4×25 cm, CHCl$_3$) to give 4.82 g of 2-methoxymethoxymethyl-3,4,5-trimethoxyaniline (89.7%) as a syrup. $^1$H-NMR (CDCL$_3$): δ3.42 (3H, s, CH$_2$OMe), 3.77, 3.80, and 3.87 (each 3H, s, 3×OMe), 4.63 and 4.66 (each 2H, s, 2×CH$_2$), 6.05 (1H, s, H-6). Analyses: Calculated for $C_{12}H_{19}NO_5$: C, 56.02; H, 7.44; N, 5.44. Found: C, 56.47; H, 7.05; N, 5.48.

By following the same procedure, but using the corresponding nitro-benzene derivatives having various O-protecting groups, the following aniline congeners of formula IV were prepared:
2-benzyloxymethyl-3,4,5-trimethoxyaniline,
2-methoxymethoxymethyl-3,5-dimethoxyaniline,
2-benzyloxymethyl-4,5-dimethoxyaniline, and
2-benzyloxymethoxymethyl-4,5-dimethoxyaniline.

Example 8

A mixture of 2-hydroxymethyl-1-nitro-3,4,5-trimethoxybenzene (200 mg, 0.82 mmol) and 10% palladium on carbon (100 mg) in ethanol (4 ml) was hydrogenated at 20 psi overnight. The mixture was filtered through a Celite pad and washed with ethanol. The combined filtrate and washings were evaporated in vacuo to dryness. The residue was chromatographed over a silica gel column (2×20 cm) using toluene/ethyl acetate (2:1, v/v) as the eluent to give 2-methyl-3,4,5-trimethoxyaniline as brown crystals (hexane), 130 mg (80%) with mp 49–51 °C. $^1$H-NMR (CDCl$_3$): δ2.01 (3H, s, Me), 3.49 (2H, b, exchangeable, NH$_2$), 3.77, 3.78, and 3.82 (each 3H, s, 3×OMe), 6.07 (1H, s, H-6). Analyses: Calculated for $C_{10}H_{15}NO_3$: C, 60.90; H, 7.67; N, 7.10. Found: C, 61.05; H, 7.46; N, 7.00.

By following the same procedure, but using the corresponding 2-hydroxy-1-nitrobenzenes, the following 2-methylanilines were prepared:
3,5-dimethoxy-2-methylaniline, and
4,5-dimethoxy-2-methylaniline.

Example 9

Sodium nitrite (150 mg, 2.1 mmol) was added to a suspension of methoxymethoxymethyl-3,4,5-trimethoxyaniline (514 mg, 2 mmol) in ice (5 g) containing concentrated hydrochloric acid (1 ml). After stirring for 25 minutes at 0 °C., a solution potassium iodide (350 mg) in water (1 ml) was added to the mixture and continuously stirred for an additional 20 minutes at room temperature. The mixture was extracted with ethyl acetate (10 ml×4), which was then washed successively with 2% sodium sulfite, water, and dried over sodium sulfate. The solvent was evaporated in vacuo, and the residue was chromatographed on a silica gel column (1×30 cm) using chloroform as the eluent to give 1-iodo-2-methoxy-methoxymethyl-3,4,5-trimethoxybenzene as a syrup. $^1$H-NMR (CDCl$_3$): δ3.46 (3H, s, CH$_2$OMe), 3.85 (6H, s, 2×OMe), 3.91 (3H, s, 1×OMe), 4.66 and 4.76 (each 2H, s, 2×CH$_2$), 7.16 (1H, s, H-6). Analyses: Calculated for $C_{12}H_{17}IO_5$: C, 39.15; H, 4.65; I, 34.47. Found: C, 39.22; H, 5.05; I, 35.09.

By following the same procedure but using the corresponding anilines, the following halobenzenes were synthesized:
1-iodo-2-benzyloxymethyl-3,4,5-trimethoxybenzene,
1-iodo-2-methoxymethoxymethyl-3,5-dimethoxybenzene,
1-iodo-2-benzyloxymethyl-3,5-dimethoxybenzene,
1-bromo-2-benzyloxymethyl-5-methoxybenzene,
1-iodo-2-methyl-3,4,5-trimethoxybenzene, and
1-iodo-2-methyl-4,5-dimethoxybenzene.

Example 10

A mixture of 4-benzyloxy-3-methoxyanthranilic acid (8.199 g, 0.03 mol), 2,3,4,5-tetramethoxy-1-iodobenzene (11.026 g, 0.033 mol), copper powder (0.48 g), cuprous oxide (0.48 g) and potassium carbonate (5.17 g) in diglyme (60 ml) was heated under reflux for 5 hours. The solvent was removed by distillation in vacuo, and the residue was triturated with 1% sodium hydroxide solution (300 ml). After filtration, the mixture was washed with ether (30 ml×3) and the aqueous alkaline solution was acidified with 6N hydrochloric acid, and then extracted with ethyl acetate (50 ml×6). The combined extracts were washed with water, dried over sodium sulfate, and evaporated in vacuo to dryness. The residue was chromatographed on a silica gel column (5×40 cm) using chloroform-methanol (50:1 v/v) as the eluent. The main fraction was collected and evaporated to give, after recrystallization from hexane-ethanol, 4-benzyloxy-3-methoxy-N-(2,3,4,5-tetramethoxyphenyl)-anthranilic acid, 8.69 g (60%); mp 138×9° C. $^1$H-NMR (CDCl$_3$): δ3.54, 3.65, 3.82, 3.93, and 3.98 (each 3H, s, 5×OMe), 5.20 (2H, s, CH$_2$), 5.99 (1H, s, H-6'), 6.89 (1H, d, J=9.0 Hz, H-5), 7.38 (5H, m, Ph), 7.94 (1H, d, J=9.0 Hz, H-6). Analyses: Calculated for $C_{25}H_{27}NO_8$: C, 63.96; H, 5.80; N, 2.98. Found: C, 64.00; H, 5.85; N, 3.01.

By following the same procedure but using the corresponding 2-halobenzoic acids (formula II) and anilines (formula IV), or anthranilic acids (formula III) and halobenzenes (formula V), the following diphenylamine carbonic acids of formula VI were prepared:
3-benzyloxy-N-(2,3,4,5-tetramethoxyphenyl)anthranilic acid,
4-nitro-N-(2,3,4,5-tetramethoxyphenyl)anthranilic acid, and
4-benzyloxy-3-methoxy-N-(2-methoxymethoxymethyl-3,4,5-trimethoxyphenyl)anthranilic acid.

Example 11

To an ice-cold solution of 2-(N-2,3,4,5-tetramethoxyphenyl)amino-4-benzyloxy-3-methoxybenzoic acid (2.40 g, 5 mmol) in dry benzene (20 ml) containing pyridine (0.408 g, 5.2 mmol) was added in one portion thionyl chloride (0.833 g, 7 mmol). The reaction mixture was stirred for 10 minutes, and then evaporated in vacuo to dryness. The residue was treated with a mixture of piperidine (1.373 g, 16 mmol) and triethylamine (1.62 g, 16 mmol) in dry benzene (10 ml) and continuously stirred for 2 hours. The mixture was diluted with benzene (50 ml), and washed successively with 1 N hydrochloric acid (20 ml×4), 10% sodium bicarbonate solution and water, and dried over sodium sulfate. The benzene solution was evaporated in vacuo to dryness, and the residue was heated with a mixture of phosphoryl chloride (3 ml) in benzene (10 ml) at reflux for 1.5 hours. The reaction mixture was concentrated in vacuo to give a red syrup, which was treated with 0.1N hydrochloric acid, and heated at 80° C. for 1 hour. After cooling to room temperature, the mixture was adjusted to pH 9 with 0.1N sodium hydroxide. The slightly alkaline solution is extracted with chloroform (20 ml×4). The combined chloroform extracts are washed with water, dried over sodium sulfate, and evaporated to dryness. The residue was chromatographed on a silica gel (3×40 cm). 6-Benzyloxy-1,2,3,4,5-pentamethoxy-9-acridone was eluted from the column with chloroform-methanol (50:1 v/v), which was recrystallized from ethanol (1.04 g, 44%); mp 130–1° C. $^1$H-NMR (CDCL$_3$): δ3.94, 3.99, 4.04, 4.05, and 4.09 (each 3H, s, 5×OMe), 5.26 (2H, s, CH$_2$), 6.93 (1H, d, J=9.0 Hz, H-7), 7.33–7.43 (5H, m, Ph), 8.09 (1H, d, J=9.0 Hz, H-8), 8.70 (1H, b, exchangeable, NH).

Analyses: Calculated for $C_{25}C_{25}NO_7$: C, 66.51; H, 5.58; N, 3.10. Found: C, 66.57; H, 5.59; N, 3.10.

By following the same procedure but using the corresponding diphenylamine carboxylic acids, the corresponding 9-acridones were prepared:

5-benzyloxy-1,2,3,4-tetramethoxy-9-acridone,
6-nitro-1,2,3,4-tetramethoxy-9-acridone, and
6-benzyloxy-1,2,3,5-tetramethoxy-4-methoxymethoxymethyl-9-acridone.

Example 12

A mixture of 6-benzyloxy-1,2,3,4,5-pentamethoxy-9-acridone (2.257 g, 5 mmol), $K_2CO_3$ (3.0 g) and methyl iodide (2.128 g, 15 mmol) in acetone (60 ml) was heated under reflux for 20 hours. After cooling to room temperature, the mixture was filtered and washed with acetone. The combined filtrate and washings are evaporated in vacuo to dryness. The residue was dissolved in chloroform (60 ml), and the solution is washed with water (30 ml×3), dried over sodium sulfate, and concentrated to dryness. The residue was crystallized from ethanol to give 6-benzyloxy-10-methyl-1,2,3,4,5-pentamethoxy-9-acridone, 2.007 g (89%), mp 127–8 °C. $^1$H-NMR (CDCl$_3$): δ3.70, 3.87, 3.91, 3.93, 3.98, and 4.10 (each 3H, s, 5×OMe, 1×NMe), 5.24 (2H, s, CH$_2$), 6.96 (1H, d, J=9.05 Hz, H-7), 7.32–7.48 (5H, m Ph), 8.01 (1H, d, J=9.05, H-8). Analyses: Calculated for $C_{25}H_{27}NO_7$: C, 66.21; H, 6.00; N, 3.09. Found: C, 65.99; H, 6.18; N, 3.11.

By following the same procedure but using the corresponding 9-acridones, the following 10-methyl derivatives were prepared:

5-benzyloxy-10-methyl-1,2,3,4-tetramethoxy-9-acridone,
6-nitro-10-methyl-1,2,3,4-tetramethoxy-9-acridone, and
6-benzyloxy-4-methoxymethoxymethyl-10-methyl-1,2,3,5-tetramethoxy-9-acridone.

Example 13

A solution of 6-benzyloxy-10-methyl-1,2,3,4,5-pentamethoxy-9-acridone (445 mg, 1 mmol) in methanol (30 ml) con concentrated hydrochloric acid (4 ml) was heated under reflux for 14 hours. After cooling to room temperature, the orange-colored crystals of 6-benzyloxy-1-hydroxy-10-methyl- 2,3,4,5-tetramethoxy-9-acridone (365 mg) that deposit were collected by filtration. An additional crop was obtained from the mother liquor to give a total of 405 mg (94%) of the product, mp 131–2 °C. $^1$H-NMR (acetone-d$_6$): δ3.79, 3.83, 3.87, 3.92, and 4.09 (each 3H, s, 4×OMe, 1×NMe), 5.34 (2H, s, CH$_2$), 7.25 (1H, d, J=9.0 Hz, H-7), 7.32–7.45 (5H, m, ph), 8.01 (1H, d, J=9.0 Hz, H-8), 14.04 (1H, s, exchangeable, OH-1). Analyses: Calculated for $C_{25}H_{25}NO_7$: C, 66.51; H, 5.58; N, 3.10. Found: C, 66.55; H, 5.53; N, 3.22.

By following the same procedure but using the corresponding 10-substituted 1-methoxy-9-acridones, the following corresponding 1-hydroxy-9-acridones of formula I were prepared:

5-benzyloxy-1-hydroxy-10-methyl-2,3,4-trimethoxy-9-acridone,
6-benzyloxy-1-hydroxy-10-methyl-2,3,4-trimethoxy-9-acridone,
7-benzyloxy-1-hydroxy-10-methyl-2,3,4-trimethoxy-9-acridone,
5-benzyloxy-1-hydroxy-10-methyl-2,3,4,6-tetramethoxy-9-acridone,
6-nitro-10-methyl-2,3,4-trimethoxy-9-acridone, and
7-nitro-10-methyl-2,3,4-trimethoxy-9-acridone.

Example 14

A mixture of 6-benzyloxy-1-hydroxy-10-methyl-2,3,4,5-tetramethoxy-9-acridone (344 mg, 0.76 mmol) in ethanol (80 ml) containing dioxane (20 ml) and 10% palladium on carbon (200 mg) was hydrogenated at 50 psi for 2.5 hours. The mixture was filtered through a pad of Celite and washed well with ethanol and chloroform. The combined filtrate and washings were evaporated in vacuo to dryness. The solid residue was recrystallized from a mixture of ethanol/hexane (2:3) to give 1,6-Dihydroxy-2,3,4,5-tetramethoxy-9-acridone, 222 mg (80.7%), mp 214–5 °C. $^1$H-NMR (DMSO-d$_6$): δ3.69, 3.75, 3.78, 3.80, and 4.02 (each 3H, s, 4×OMe, 1×NMe), 6.94 (1H, d, J=9.0 Hz, H-7), 7.84 (1H, d, J=9.0 Hz, H-8), 10.45 (1H, exchangeable, OH-6), 14.18 (1H, exchangeable, OH-1). Analyses: Calculated for $C_{18}H_{19}NO_7$: C, 59.83; H, 5.30; N, 3.88. Found C, 60.00, H, 5.38; N, 4.00.

By following the same procedure but using the corresponding O-protected N-substituted 1-hydroxy-9-acridones, the following compounds of formula I were prepared:

1,6-dihydroxy-2,3,4,5-tetramethoxy-10-methyl-9-acridone,
5-dihydroxy-10-methyl-2,3,4-trimethoxy-9-acridone,
1,6-dihydroxy-10-methyl-2,3,4-trimethoxy-9-acridone,
1,7-dihydroxy-10-methyl-2,3,4-trimethoxy-9-acridone, and
2-amino-3-(1,6-dihydroxy-2,3,4,5-tetramethoxy-9-acridone-1-yl)propionic acid.

DISCUSSION

It was found that multisubstituted 1-hydroxy-N-methyl-9-acridones bearing substituents at the 2,3,4,5, and 6 positions inhibited over 90% of prelabeled precursor incorporation into DNA and possessed significant inhibition of leukemic HL-60 cell growth in vitro. Generally, 9-acridones without substituents such as methoxy or phenyl function at position 4 exhibited no anticancer activity. These findings suggest that the substituent(s) (OH, or OMe) at the $R^5$, $R^6$, and $R^7$ positions of the 1-hydroxy-9-acridone molecule, the functionality at the position 4, and the formation of the intramolecular hydrogen bond between the carbonyl and the perihydroxy function may play an important role in their antitumor activity.

We have been able to synthesize sufficient amounts of TSA-35 and acronycine to enable us for the first time to provide for in vivo comparative antitumor studies (see Table 1). It was found that TSA-35 exhibited marked anticancer activity. For example, TSA-35 produced an increase in life span (ILS) of 42% and >92%, respectively, of C57BL/6 mice bearing Lewis lung carcinoma when given TSA-35 at dose levels of 25 and 50 mg/kg daily for 4 days i.p. At these dose levels, TSA-35 was found to be non-toxic to C57BL/6 mice. At the same dose levels, acronycine increased life-span by 40% and 40%, respectively. There were 2 out of 5 long term survivals at 50 mg/kg for TSA-35. For carcinoma E07713, acronycine 100 mg/kg daily for 4 days i.p. resulted in 1 out of 3 toxicity-induced deaths but no deaths were observed as a consequence of administration of TSA-35. At 50 mg/kg and 100 mg/kg, TSA-35 increased life-span 17% and >39% (with 1 out of 3 long term survival), respectively, and acronycine increased life-span by 26% and 4% (although toxic), respectively.

On the basis of the above findings, we developed a hypothesis that 1-hydroxy-9-acridones bearing electron-donating function(s) (such as OH, alkyloxy, $NH_2$,) or electron-withdrawing group(s) (such as $NO_2$ or halogen) at the $R^5$, $R^6$, and $R^7$ positions and substituents (such as alkyloxy, $CH_3$m $CH_2OH$ and its N-alkyl-carbamate) at the $R^4$ position, may have potent antitumor activity.

TABLE 1

Comparison of Chemotherapeutic Effects of Acronycine and TSA-35 against Solid Tumors in Mice

| Compounds | Dose (mg/kg, ip Day 1 QDX4) | Lewis Lung Carcinoma | | | E07713 Mammary Adenocarcinoma | | | B-16 Melanoma | | |
|---|---|---|---|---|---|---|---|---|---|---|
| | | Day 7 BWC* (g) | % ILS+ | N/T | Day 7 BWC(g) | % ILS | N/T | Day 7 BWC(g) | % ILS | N/T |
| Acronycine | 0 | +0.6 | NA | 0/30 | +1.4 | NA | 0/5 | +0.8 | NA | 0/5 |
| | 25 | −0.6 | 40 | 0/5 | — | — | — | — | — | — |
| | 50 | −0.5 | 34 | 0/15 | +0.4 | 26 | 0/5 | −0.6 | 24 | 0/5 |
| | 100 | 5/5 death | NA | 0/5 | 1/3 death | 4 | 0/3 | — | — | — |
| TSA-35 | 25 | +0.2 | 42 | 0/5 | +0.6 | 17 | 0/5 | +0.2 | 31 | 0/5 |
| (glyfoline) | 50 | +0.3 | >59 | 2/15 | +0.3 | >95 | 1/3 | +0.4 | 40 | 0/5 |
| | 100 | +0.5 | >46 | 1/10 | — | — | — | — | — | — |
| | 150 | −0.3 | >79 | 2/8 | — | — | — | −1.0 | >56 | 1/5 |

*Body weight changes
+Percent increase in life-span
Number of 40 day tumor-free mice/total number of mice bearing tumor

What is claimed is:

1. A method for synthesizing a compound having the structure:

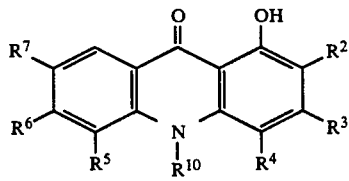

(I)

wherein
$R^2$ and $R^3$ are the same or different and are hydrogen, a saturated or unsaturated alkyl group having 1 to 5 carbon atoms, a hydroxy group, a saturated or unsaturated alkyloxy group having 1 to 5 carbon atoms, an O-alkyloxyalkyl group wherein each alkyl is the same or different having 1 to 5 carbon atoms, an O-benzyloxyalkyl group with the alkyl having 1 to 5 carbon atoms, an O-acetyl group, an O-benzoyl group, or an O-benzyl group;

$R^4$ is hydrogen, a saturated or unsaturated alkyl group having 1 to 5 carbon atoms, a hydroxy group, a hydroxymethyl group, a saturated or unsaturated alkyloxy group having 1 to 5 carbon atoms, an O-alkyloxyalkyl group wherein each alkyl is the same or different having 1 to 5 carbon atoms, an O-benzyloxyalkyl group with the alkyl having 1 to 5 carbon atoms, an O-alkyloxyalkyloxyalkyl group wherein each alkyl is the same or different having 1 to 5 carbon atoms, an O-acetyl group, an O-benzoyl group, or an O-benzyl group;

wherein
$R^5$, $R^6$ and $R^7$ are the same or different and are hydrogen, a saturated or unsaturated alkyl group having 1 to 5 carbon atoms, sulfate, phosphate, a hydroxy group, a saturated or unsaturated alkyloxy group having 1 to 5 carbon atoms, an O-alkyloxyalkyl group wherein each alkyl is the same or different having 1 to 5 carbon atoms, an O-benzyloxyalkyl group with the alkyl having 1 to 5 carbon atoms, an O-acetyl group, an benzoyl group, a nitro group, an amino group, an N-alkylamino group having 1 to 5 carbon atoms, an N,N-dialkylamino group with each alkyl having 1 to 5 carbon atoms, an aminoalkyloxy group having 1 to 5 carbon atoms, an N-alkyl-aminoalkyloxy group wherein each alkyl is the same or different having 1 to 5 carbon atoms, an N,N-dialkyl-aminoalkyloxy group wherein each alkyl is the same or different having 1 to 5 carbon atoms, a quaternary ammonium alkyloxy salt, or a halogen; and $R^{10}$ is hydrogen, a saturated or unsaturated alkyl group having 1 to 5 carbon atoms, aminoalkyl group having 1 to 5 carbon atoms, an N-alkylaminoalkyl group wherein each alkyl is the same or different having 1 to 5 carbon atoms, an N,N-dialkylaminoalkyl group wherein each alkyl is the same or different having 1 to 5 carbon atoms, or an amino acid moiety;

which comprises:

(a) combining a compound having the structure:

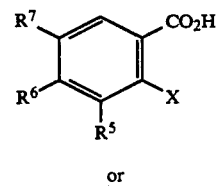

(II)

or

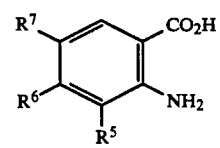

(III)

wherein $R^5$, $R^6$ and $R^7$ are the same as defined previously; and
X is F, Cl, Br, or I;
with a compound having the structure:

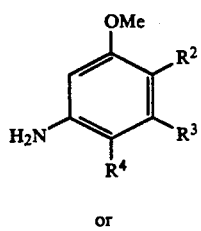

or

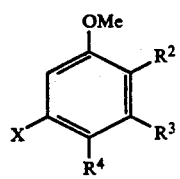

respectively, wherein the molar ratio of the compound of formula II to the compound of formula IV or of the compound of formula III to the compound of formula V is about 1 to 5 and $R^2$, $R^3$ and $R^4$ are the same as defined previously; and X is F, Cl, Br, or I or a nitro group;

under Ullman condensation conditions so as to form a compound having the structure:

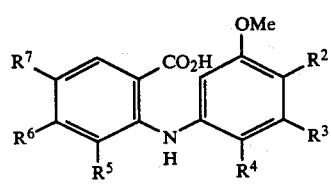

wherein $R^2$, $R^3$, $R^4$, $R^5$, $R^6$, and $R^7$ are the same as defined previously;

(b) treating the compound formed in step (a) under cyclization conditions so as to form a compound having the structure:

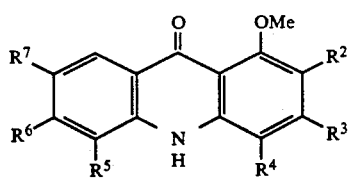

wherein $R^2$, $R^3$, $R^4$, $R^5$, $R^6$, and $R^7$ are the same as defined previously;

(c) treating the compound formed in step (b) under N-alkylating conditions so as to form a compound having the structure:

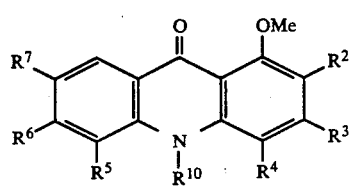

wherein $R^2$, $R^3$, $R^4$, $R^5$, $R^6$, $R^7$ and $R^{10}$ are the same as defined previously; and (d) treating the compound formed in step (c) under de-O-methylating conditions so as to form a compound having the structure:

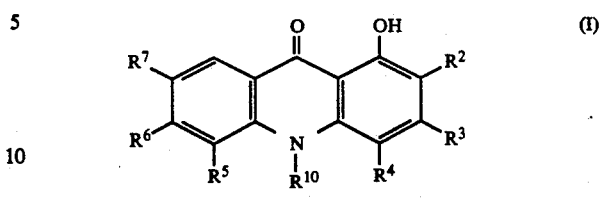

wherein $R^2$, $R^3$, $R^4$, $R^5$, $R^6$, $R^7$ and $R^{10}$ are the same as defined previously.

2. A method of claim 1, wherein in step (a) the contacting comprises the Ullman condensation of the compound of formula II with the compound of formula IV.

3. A method of claim 1, wherein in step (a) the contacting comprises the Ullman condensation of the compound of formula III with the compound of formula V.

4. A method of claim 1, wherein in step (a) the Ullman condensation conditions comprise combining the compound of formula II and the compound of formula IV or the compound of formula III and the compound of formula V in a mixture of copper, copper oxide, potassium carbonate, in a solvent with a boiling point above 110° C., at a temperature range of 100° C. to 200° C. for a period of 1 hour to 2 days.

5. A method of claim 4, wherein in step (a) the temperature range is from 120° C. to 170° C.

6. A method of claim 1, wherein in step (a) the molar ratio of the compound of formula II to the compound of formula IV is 1 to 1.5.

7. A method of claim 1, wherein in step (a) the molar ratio of the compound of formula III to the compound of formula V is 1 to 1.5.

8. A method of claim 1, wherein the step (b) the cyclization conditions comprise reacting the compound formed in step (a) with an inorganic acid at a temperature range of 60° C. to 100° C. for a period of 20 minutes to 5 hours.

9. A method of claim 8, wherein the inorganic acid is sulfuric acid or polyphosphoric acid.

10. A method of claim 1, wherein in step (b) the cyclization conditions comprise reacting the compound formed in step (a) with phosphoryl chloride followed by acid hydrolysis.

11. A method of claim 1, wherein in step (b) the cyclization conditions comprise the formation of a reaction mixture comprising the compound formed in step (a), thionyl chloride and pyridine in chloroform for 15 minutes to 2 hours, evaporating the reaction mixture to form a residue, treating the residue so formed with piperidine and triethylamine to form a piperidide derivative, and treating the piperidide derivative so formed with phosphoryl chloride followed by acid hydrolysis.

12. A method of claim 1, wherein the step (c) the N-alkylating conditions comprise combining the compound formed in step (b) with an alkylhalide in a base.

13. A method of claim 12, wherein the alkylhalide is methyl iodide or ethyl iodide.

14. A method of claim 12, wherein the base is potassium carbonate in acetone, potassium carbonate in dimethylformamide, or sodium hydride in dimethylformamide.

15. A method of claim 1, wherein in step (d) the de-O-methylating conditions comprise combining the compound formed in step (c) with an acid in an alcohol or a boron trihalide in an ethereal solution at a temperature range of 40° C. to 140° C. for a period of 0.5 hours to 2 days.

16. A method of claim 15, wherein the acid is hydrochloric acid, hydrobromic acid, sulfuric acid, or phosphoric acid and the alcohol is methanol, ethanol, or propanol.

17. A method of claim 15, wherein the boron trihalide is boron trifluoride, boron trichloride, or boron tribromide.

* * * * *